United States Patent [19]

Erskine et al.

[11] Patent Number: 4,714,931
[45] Date of Patent: Dec. 22, 1987

[54] INK JET PRINTING SYSTEM

[75] Inventors: William G. Erskine; Richard J. Marsden, both of Cambridgeshire, England

[73] Assignee: Domino Printing Sciences PLC., Cambridge, England

[21] Appl. No.: 940,094

[22] Filed: Dec. 10, 1986

[30] Foreign Application Priority Data

Dec. 16, 1985 [GB] United Kingdom ............... 8530885

[51] Int. Cl.$^4$ .................... G01D 15/18; E03B 5/00
[52] U.S. Cl. .................................. 346/75; 346/140 R; 137/566
[58] Field of Search ............. 346/75, 140 R; 137/566, 137/567, 568

[56] References Cited

U.S. PATENT DOCUMENTS 3,761,953  9/1973  Helgeson et al. ............... 346/75
4,121,222  10/1978  Diebold et al. .................. 346/75
4,527,170  7/1985  Iwasari et al. .................. 346/75
4,555,709  11/1985  Greeson ...................... 346/1.1 X Primary Examiner—E. A. Goldberg
Assistant Examiner—Gerald E. Preston
Attorney, Agent, or Firm—Robbins & Laramie

[57] ABSTRACT

In a continuous ink jet printing system a viscosity determining means (12) has a measuring tank (29). An inlet (32) to the tank is connected to the system ink circuit to receive ink under pressure and the inlet has a flow restriction. A vent/return pipe (34) vents the tank and enables ink to be returned to the reservoir. An outlet (33) drains ink from the tank and returns it to the pump, the outlet including a valve (13) to open and close the outlet. A level detector (30,31) in the tank is connected to a timer (38) to determine the time taken for the tank to fill from a first level to a second level detected by the level detector and hence to provide a representation of viscosity of the ink.

6 Claims, 5 Drawing Figures

INK JET PRINTING SYSTEM

DESCRIPTION

The present invention relates to a continuous ink jet printing system and in particular to a means of measuring the viscosity of ink in the system during use.

In a continuous ink jet printing system ink is passed from a reservoir to a print head under pressure, the ink being forced through a nozzle and broken up into droplets which are charged according to the desired print position, the charged droplets then being deflected onto the target by an electrostatic field. Uncharged droplets are returned to the reservoir. During operation of the printer volatile solvents are lost from the ink due to evaporation so that the composition and physical properties of the ink change with time. It is known therefore to measure the viscosity of the ink and to introduce solvents into the ink to maintain the desired viscosity.

In one known method, what is known as a "falling ball viscometer" is used, an upright tube being connected to a supply line for the ink and an element movable upwardly and downwardly within the tube being provided. A valve is positioned to control the flow of liquid from the supply line to the tube and a control means is arranged to open the valve to allow upwards flow of liquid in the tube sufficient to move the element to an upper part of the tube, subsequently closing the valve so as to terminate the upwards flow of liquid, and sensors being used to determine the time taken for the element to descend through a predetermined distance through the liquid within the tube. The time taken for the element to fall a known distance is representative of the viscosity of the liquid. Depending on the time measured so the ink is charged with a component which causes a change in the viscosity to correct the difference between the measured viscosity and the desired viscosity.

In this method the clearance between the falling ball and the fluted wall of the tube is only a few microns and particles of ink and/or agglomerates of pigments or foreign bodies, if present, can seriously impede the free movement of the ball as it passes through the liquid thus causing incorrect measurement.

According to the present invention a continuous ink jet printing system which comprises an ink circuit including an ink reservoir; a pump; a nozzle from which a continuous stream of ink droplets is projected in use under pressure from the pump; a device for collecting unused droplets; and a recirculation circuit for returning unused ink to the ink reservoir, further includes a means for determining the viscosity of the ink at selected intervals, the viscosity determining means having a measuring tank; an inlet to the tank connected to the ink circuit to receive ink under pressure, the inlet having a flow restriction; a vent/return pipe to vent the tank and enable ink to be returned to the reservoir; an outlet for draining ink from the tank and returning it to the pump, the outlet including a valve to open and close the outlet; a level detector in the tank; and a timer to determine the time taken for the tank to fill from a first level to a second level detected by the level detector and hence to provide a representation of the viscosity of the ink.

Preferably, the temperature of the ink is monitored and the measured flow time is compared with the theoretical flow time at that temperature and if significantly different the viscosity of the ink is varied to bring it within range.

Preferably, a means is provided for charging the ink with a component which causes a change in the viscosity to maintain the desired viscosity, the charging means being controlled in dependence upon the time determined by the timer.

The invention also includes a continuous ink jet printing method using such a system, in which, at selected intervals, a valve in the outlet from the measuring tank is first opened to allow the tank to be emptied, and then closed to allow the tank to fill; a first signal is provided when the level of ink in the tank reaches a first level; a second signal is provided when the level of liquid in the tank reaches a second level; the time taken for the ink level to rise from the first level to the second level is measured and the outlet valve from the measuring tank is then opened to lower the level of ink in the tank to a level below the first level.

A temperature sensing transducer may be provided in or near the inlet to the measuring tank to provide a signal indicative of the ink temperature, which signal may be sent to a microprocessor together with a signal indicative of the viscosity (a signal derived from the time taken for the tank to fill from the first to the second level), in order to provide a control signal to control the viscosity the ink.

In addition a pressure sensing transducer may be provided in or near the inlet to the measuring tank to provide a signal indicative of the ink pressure, which signal may be sent to a microprocessor together with a signal from the viscometer of the filling time and a signal indicative of the temperature of the ink, in order to allow the microprocessor to accurately calculate the viscosity of the ink, and compare this with the required viscosity which is stored in memory. A control signal is sent to control charging of the viscosity adjusting component into the ink.

A particular advantage of this apparatus and method is that the pressure of ink supplied to the nozzle is regulated at about 40 psi ($2.76 \times 10^5$ Pa) so that ink at this pressure can be fed to the viscometer. For a given temperature, experiment has shown that pressure variations as high as 5 psi ($3.45 \times 10^4$ Pa) lead only to a maximum calculated viscosity variation of about $5.6 \times 10^{-4}$ Pa.-s—within the limits required for consistent print quality. The, if desired, measurement of actual pressure can be dispensed with as far as the viscosity measuring part of the system is concerned.

One example of a system constructed in accordance with the present invention will now be described with reference to the accompanying drawing in which.

Figure 1:
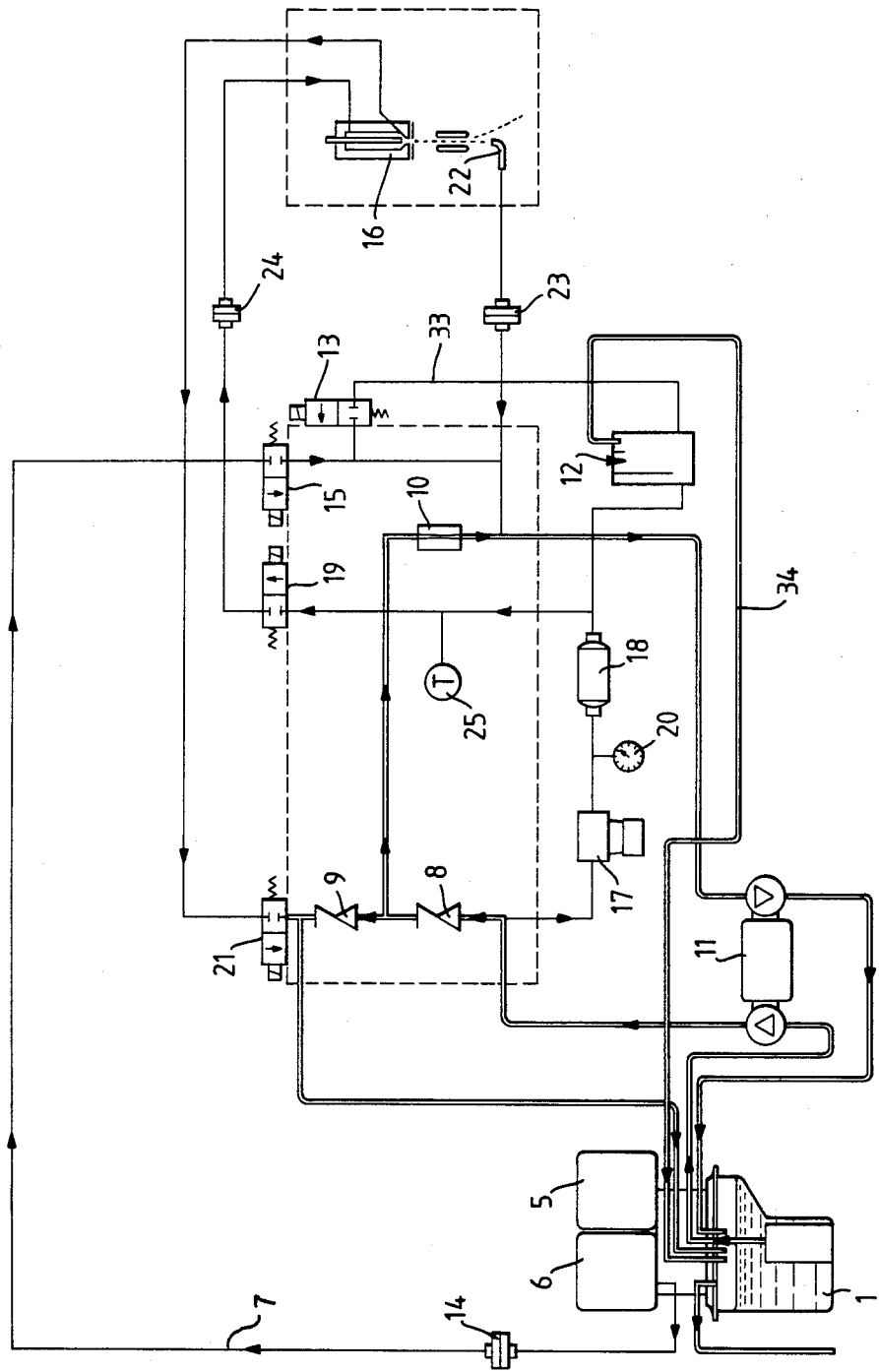
FIG. 1 illustrates, schematically, an ink jet printing system.

The ink system shown in FIG. 1 conveys ink from an ink reservoir 1 to a print head assembly which includes a nozzle head 16 and a gutter 22 by means of which drops which are not used for printing are returned to the ink system.

The reservoir 1 is topped up from an ink cartridge 5 which can be replaced when empty and which provides top-up to the ink reservoir 1. A make-up cartridge 6 contains solvents which can be added to the ink to make up for loss of solvent due to evaporation from non-printed droplets returned through the gutter 22. The make-up cartridge feeds solvents through a filter 14 on demand via a line 7 through a solenoid valve 15 to the main return line from the gutter 22.

Continuous ink jet printing is well known and the system will not be described in detail, but in brief the nozzle assembly 16 includes a piezo-electric transducer (not shown) which breaks a flow of ink into individual droplets which are then electrostatically charged by a variable amount in order to suit the desired print position on the target, unprinted drops being substantially uncharged. The stream of droplets passes between a pair of deflection electrodes, the electric field between which causes the charged droplets to be deflected by appropriate amounts and into their desired positions on target. The levels of charge on the individual droplets are controlled by a print microprocessor (not shown in FIG. 1).

From the ink reservoir 1 the ink is passed by means of a double-ended pump 11 through a pressure relief valve 8 (to ensure that the ink pressure does not rise above 60 psi ($4.14 \times 10^5$ Pa) in the line to the head assembly), ink for printing being led off between the double ended pump and the pressure relief valve 8 through a manually adjustable pressure regulator 17 (the pressure being monitored by an operator through a gauge 20 or sensed automatically by a pressure transducer 25), through a further filter 18, through a feed solenoid 19 and a further filter 24 to the nozzle assembly 16. A bleed line is provided from the nozzle head 16 to return a mixture of ink and entrained air from the head at start-up and shut-down, this being achieved through a bleed solenoid 21.

On the return side ink is passed through a bleed control orifice 10 back to the double ended pump 11 and thence to the ink reservoir again. This ensures that the pump applies sufficient suction and is adequately lubricated, the bleed control orifice being preset to allow a predetermined flow of ink to the pump. The junction between the pressure release valve 8 and the line to the bleed control orifice 10 is connected back to the reservoir via a further pressure relief valve 9 which opens if the pressure of ink in the bleed line exceeds 1 psi ($7.15 \times 10^3$ Pa) inch.

The operation of the pump motor and the various valves is controlled by a further microprocessor (not shown) linked to the print microprocessor. The ink control system (see FIG. 4) for the system needs to monitor solvent loss and this is achieved indirectly by monitoring the viscosity of the ink. A viscometer 12 is provided, receiving ink from the same filter 18 through which ink is passed to the head assembly.

The viscometer has an overflow/vent pipe 34 which leads back to the reservoir 1. The outlet from the viscometer is at a level above that of the inlet to allow ink to remain in the base of the viscometer and keep the capillary tube continuously wetted with ink.

The ink jet printer may have several print heads linked to a common ink supply.

From theoretical considerations of the flow of liquid through a vertical capillary, viscosity at standard temperature can be deduced from the following:

$$\eta = \frac{\pi d^4 \Delta P t}{128 L V} \quad (1)$$

where:
 $\eta$=dynamic viscosity (Pa.s)
 d=capillary diameter (mm)
 $\Delta P$=pressure drop across the capillary (Pa)
 t=time (sec) for a volume of liquid V(mm$^3$) to flow
 L=length of tube (mm)

The above equation assumes that at the exit of the tube the stream has no energy. In most cases this is not the case, and the source of this energy is the pressure applied to the fluid. This can be corrected for by the addition of a second term to the equation giving:

$$\eta = \frac{\pi d^4 \Delta P t}{128 L V} - \frac{aVp}{8\pi L t^m} \quad (2)$$

where:
 a=constant approximately equal to 1
 $\rho$=density
 m=$\frac{2}{3}$ for square ended capillaries and 2 for trumpet shaped ends Under certain conditions, long flow times for example, the energy correction can be ignored. Other correction terms can compensate for end effects, elastic deformation, turbulence etc. but are insignificant in this application.

Thus, it will be appreciated that with all other terms remaining substantially constant, a measurement of the time t can provide an indication of the viscosity of the liquid.

Figure 2:
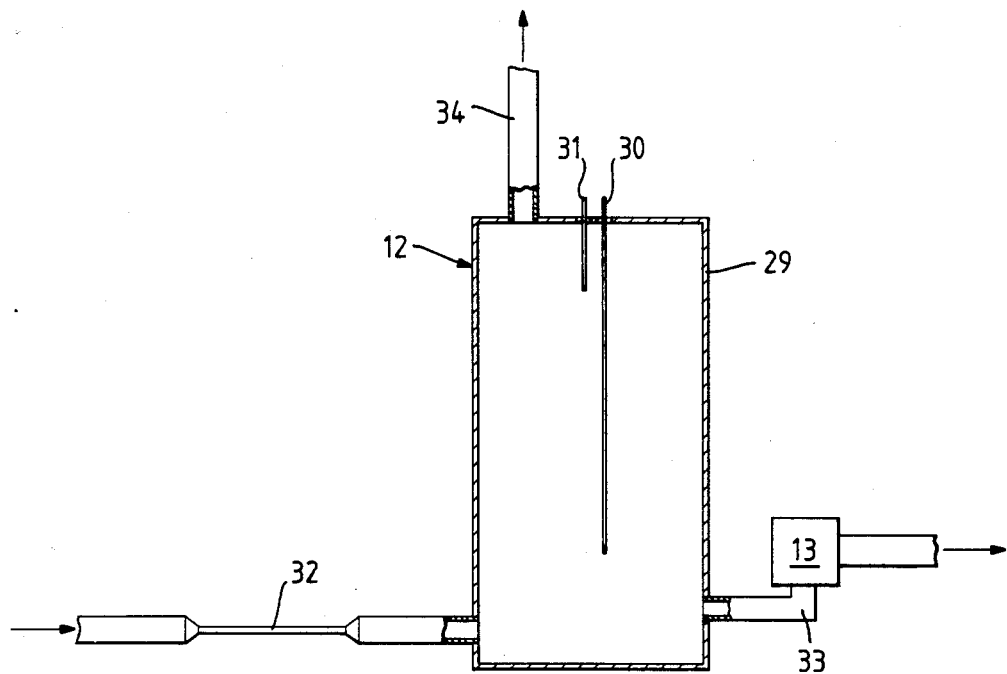
FIG. 2 illustrates a viscometer therefor.

In an ink jet printing system as described above the ink is pressurized by the pump 11. The viscometer 12 used in this example has a container 29 with a pair of level sensors 30,31 to which a voltage is applied. Ink is fed into it through a flow restricting orifice capillary 32 (see FIG. 2). As the ink and housing are electrically conductive, when a current flows between the lower level sensor 30 and the housing the liquid is at the lower level. When there is current flow between the upper rod 31 and the housing the liquid is at the level of the upper rod. The time taken for the viscometer container to fill from the first sensor level 30 to the second sensor level 31 can thus be determined and is monitored by the control system CPU 38 (FIG. 4) to provide a measure of the viscosity (as described below). When the level of ink reaches the top sensor 31 the CPU 38 causes the viscometer solenoid 13 to be opened in a line 33 back to the pump 11 so that the double ended pump 11 sucks ink from the viscometer prior to the measuring cycle starting again. Dependent upon the level of viscosity sensed by the control system signals are sent into the make-up solenoid 15 in order to allow solvents to be added to the ink to replace those lost through evaporation.

Figure 3:
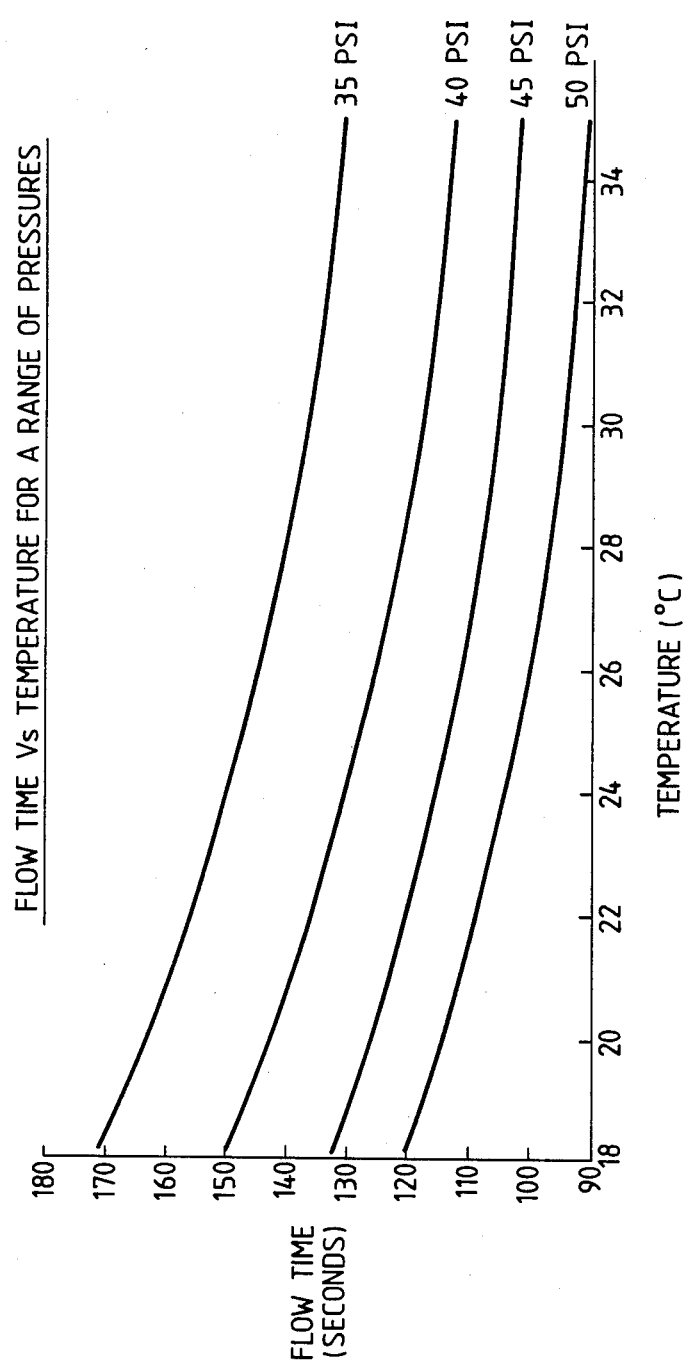
FIG. 3 is a graph of fluid flow time through a capillary and temperature for various constant pressures.

It will be appreciated that the viscosity varies with temperature and this can be seen from FIG. 3 in which the flow times, through a capillary of length L=46 mm and diameter d=0.15 mm, of a printing ink are shown plotted against temperature for a range of different pressures.

Figure 4:
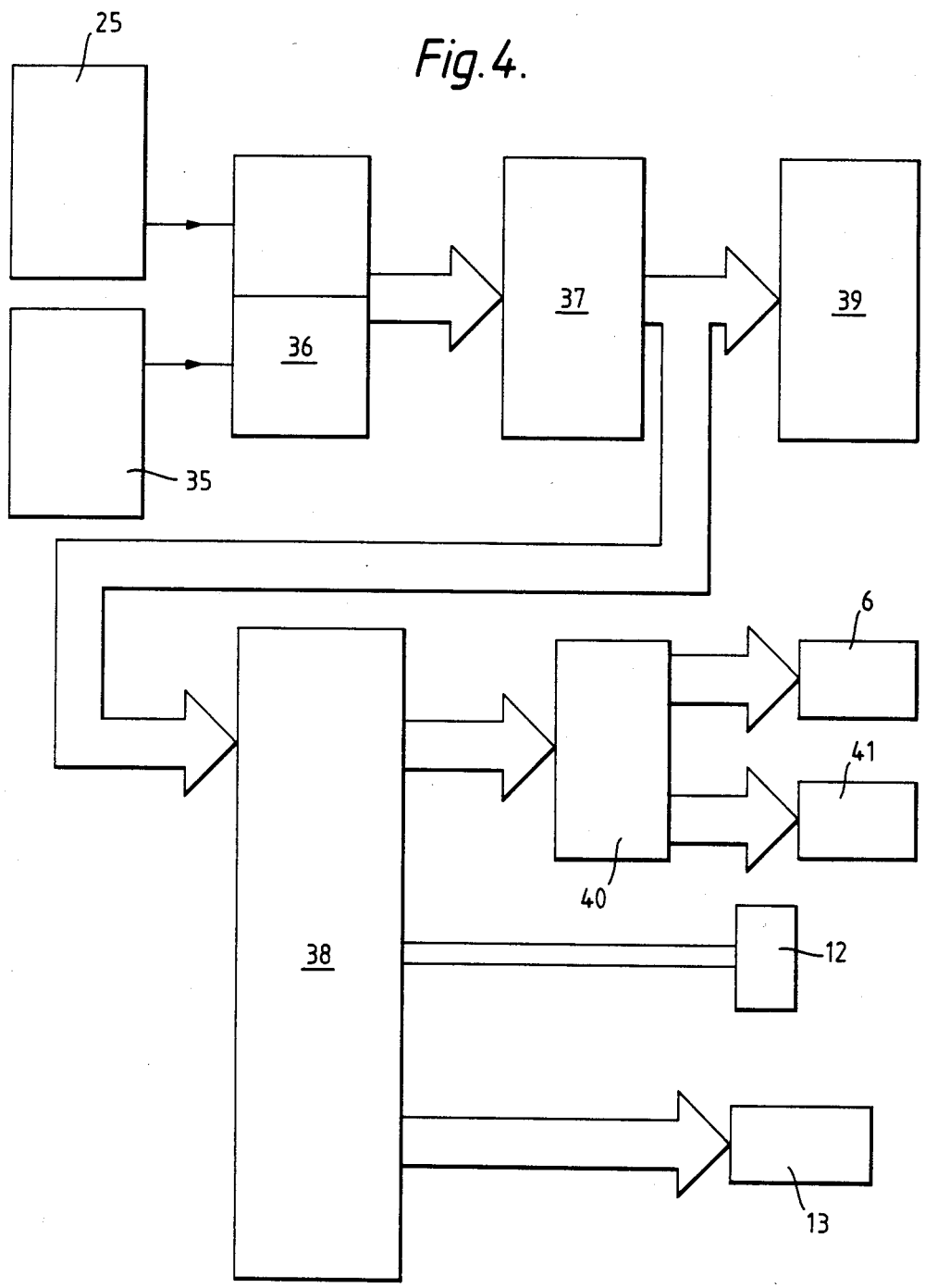
FIG. 4 shows schematically, a block diagram of the viscosity measuring and control system; and, FIG. 5 is a flow chart of viscosity measuring and control system.

The control system indicated in block diagram format in FIG. 4 includes the pressure transducer 25 and a temperature sensor 35. Pressure and temperature signals are fed through an analogue/digital convertor 36 which can be pre-calibrated as required and the signals are then latched by means of a latch 37 through to the microprocessor CPU 38 under the control of suitable software residing in the system. The control system contains a PROM in which reside plural tables of flow time values for given temperatures and supply pressures so that the flow time in the viscometer measured by the CPU 38 can be corrected for measured temperature and pressure.

The viscometer 12 is connected to the CPU 38 so that the level signals therefrom are passed to the CPU and the time measured, so that, after combination with the pressure and temperature signals and the information contained in the look-up tables in the PROM 39, the CPU can generate control signals by way of an interface 40 to the make-up solenoid 15. At the same time, signals from the interface 40 can be fed to suitable lamp displays 41 to indicate the state of operation of the viscometer.

Operation of the viscometer is under CPU control, the primary control being the output solenoid 13. The output signal from the CPU which is fed to the makeup solenoid 15 can thus be highly accurate, being corrected for temperature and pressure variations as required, and thus the correct amount of solvent can be added to the ink system.

Alternatively, a pressure relief valve can be used to supply a constant pressure of ink to the inlet to the measuring tank 32 (FIG. 2) and in this case a pressure transducer will not be required, nor will the memory need to contain pressure-related data.

Figure 5:
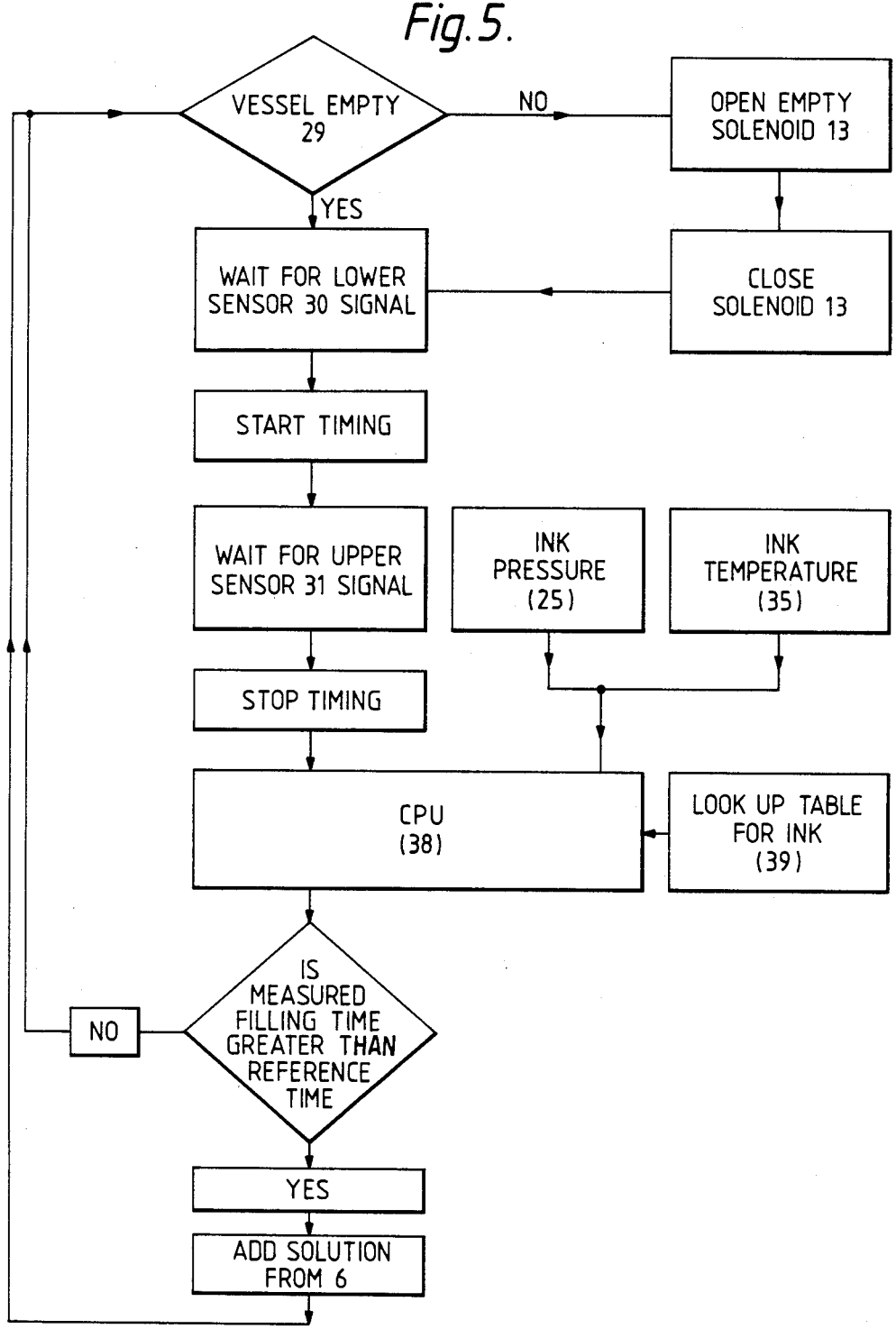

The operation of the solenoid 15 follows the flow chart shown in FIG. 5, by means of which the filling and subsequent emptying of the tank 29 is controlled by the CPU 38 in order that viscosity is determined at appropriate intervals during the operational cycle, and, if necessary, solvent added to the ink to bring it to the desired viscosity.

We claim:

1. A continuous ink jet printing system comprising
(1) an ink circuit, said circuit having:
    (a) an ink reservoir;
    (b) a pump;
    (c) a nozzle from which a continuous stream of ink droplets is projected in use under pressure from said pump;
    (d) a device for collecting unused droplets;
    (e) a recirculation circuit for returning unused ink to said ink reservoir; and,
(2) means for determining the viscosity of said ink at selected intervals, wherein said viscosity determining means has
    (i) a measuring tank;
    (ii) an inlet to said tank connected to said ink circuit to receive ink under pressure, said inlet having a flow restriction;
    (iii) a vent/return pipe to vent said tank and enable ink to be returned to said reservoir;
    (iv) an outlet for draining ink from said tank and returning it to said pump, said outlet including a valve to open and close said outlet;
    (v) a level detecting means in said tank;
    (vi) a timing means to measure the time taken for said tank to fill from a first level to a second level detected by said level detecting means; and
    (vii) means for providing a signal representative of the viscosity of said ink.

2. A system according to claim 1, wherein the temperature of said ink is monitored, and including means for comparing said measured time with a theoretical flow time at the said temperature and means for adjusting the viscosity of said ink in response to said comparison.

3. A system according to claim 1, further comprising means for charging said ink with a component which causes a change in the viscosity to maintain the desired viscosity, said charging means being controlled in dependence upon the time determined by said timer.

4. A system according to claim 1, in which a temperature sensing transducer is provided at said inlet to said measuring tank to provide a signal indicative of the ink temperature, and including a microprocessor; means for passing said signal to said microprocessor; means for passing a signal indicative of the viscosity of said ink to said microprocessor, said microprocessor being adapted to provide a control signal to control said viscosity.

5. A system according to claim 4, in which a pressure sensing transducer is provided at said inlet to said measuring tank to provide a pressure signal indicative of ink pressure; means for passing said pressure signal to said microprocessor; said microprocessor being adapted to accurately calculate the viscosity of said ink, on receipt of said signals and compare this with a predetermined required viscosity.

6. A continuous ink jet printing method using a system according to claim 1, in which, at selected intervals, said valve in said outlet from said measuring tank is first opened to allow said tank to be emptied and then closed to allow said tank to fill; a first signal is provided when the level of ink in said tank reaches a first level; a second signal is provided when the level of liquid in the tank reaches a second level; the time taken for the ink level to rise from said first level to said second level is measured and said outlet valve from the measuring tank is then opened to lower the level of ink in said tank to a level below said first level.

* * * * *